(12) United States Patent
Brucker

(10) Patent No.: US 6,770,263 B1
(45) Date of Patent: Aug. 3, 2004

(54) COMPOSITIONS AND METHODS FOR THE TREATMENT OF ACHES AND PAINS

(75) Inventor: Donald Brucker, La Jolla, CA (US)

(73) Assignee: NatureWell, Incorporated, La Jolla, CA (US)

( * ) Notice: Subject to any disclaimer, the term of this patent is extended or adjusted under 35 U.S.C. 154(b) by 73 days.

(21) Appl. No.: 10/262,477

(22) Filed: Sep. 30, 2002

Related U.S. Application Data

(60) Provisional application No. 60/326,598, filed on Oct. 1, 2001.

(51) Int. Cl.[7] ............................. A61K 9/12; A61K 9/72; A61K 31/60
(52) U.S. Cl. ......................... 424/45; 424/434; 424/435; 518/958
(58) Field of Search .......................... 424/45, 434, 435; 514/958

(56) References Cited

U.S. PATENT DOCUMENTS

| | | |
|---|---|---|
| 5,171,571 A | 12/1992 | Stephan et al. |
| 5,621,005 A * | 4/1997 | Gowan, Jr. .................. 514/557 |
| 6,068,999 A | 5/2000 | Hendrix |
| 6,103,218 A | 8/2000 | Brucker et al. |
| 6,312,736 B1 | 11/2001 | Kelly et al. |
| 6,423,697 B1 | 7/2002 | Friedman |

OTHER PUBLICATIONS

Eaton, "Butterbur Herbal Help for Margarine", *Nature Pharmacy*, Oct. 1998, pp. 22–24.
Krivoy et al., "Effect of Salicis Cortex Extract on Human Platelet Aggregation", *Planta Med.*, 67 (2001), pp. 209–212.
Kwok et al., "The anti–inflammatory natural product parthenolide from the medicinal herb Feverfew directly binds to and inhibits IkB kinase," *Chemistry & Biology*, 8 (2001), pp. 759–766.
Schmid et al., "Pharmacokinetics of salicin after oral administration of a standardised willow bark extract," *Eur. J. Clin. Pharmacol.*, (2001), 57:387–391.

* cited by examiner

*Primary Examiner*—Thurman K. Page
*Assistant Examiner*—Mina Haghighatian
(74) *Attorney, Agent, or Firm*—Fish & Richardson P.C.

(57) ABSTRACT

Provided are methods and compositions useful for treating/ aches and/or pains. The compositions comprise an aqueous medium having dispersed or dissolved therein an herbal therapeutic agent and/or an analgesic agent, wherein the composition is effective when delivered to the mucosal membrane.

26 Claims, No Drawings

COMPOSITIONS AND METHODS FOR THE TREATMENT OF ACHES AND PAINS

CROSS-REFERENCE TO RELATED APPLICATIONS

The present application claims the benefit of priority under 35 U.S.C. §119 to provisional application Ser. No. 60/326,598, filed Oct. 1, 2001, the disclosure of which is incorporated herein by reference.

TECHNICAL FIELD

This invention relates to compositions and methods for treating aches and/or pains, and more particularly to herbal compositions for pain relief associated with headaches.

BACKGROUND

Aches, pains, and discomfort are common problems for the sick, aged, and injured. For example, headaches are a common problem worldwide with the most severe being associated with migraine headaches. Women are three times more likely to be affected by migraine headaches than men. Migraine headaches occur in approximately 12% of the world's population. Thus, in the United States there are approximately 30 million people who suffer from this affliction each year. Current treatments for migraines and headaches in general utilize oral compositions that make their way through the gastrointestinal tract to the circulatory system and ultimately across the blood brain barrier. Such a traversal of the various organs in the body results in a depletion of the active ingredients in such medications through metabolism in the liver and breakdown in the stomach and intestine by acids and enzymes. Other treatments include subcutaneous injections and nasal sprays. Subcutaneous injections are painful and difficult to administer. The use of some migraine treatments such as "triptans", which are selective seratonin agonists, may cause serious side effects and are contra-indicated with certain conditions such as hypertension (Bartleson, J D, Mayo Clin. Proc., 74:702–708, 1999; Pauwels and John, Clin. Neuropharmacol., 22(3):123–136, 1999). In addition, the acute treatment of migraines with many abortive therapies may result in a "rebound effect" (Pauwels and John, Clin. Neuropharmacol., 22(3):123–136, 1999). Furthermore, migraine headaches are typically treated after they have become painful, i.e., the treatment is often ineffective in eliminating and/or in preventing the onset of the migraine headache.

The exact cause of migraine headaches is unknown. Symptoms associated with such headaches include recurring unilateral throbbing headaches, only partially preceded by a warning visual aura, nausea, vomiting, and photosensitivity. It is believed that migraines may be at least partially caused by cerebral arterial vasospasms and general cerebral inflammation. Serotonergic circuitry in the brainstem may also be involved along with activation of the trigeminovascular pain system.

SUMMARY

The invention provides a composition comprising an aqueous medium having dispersed or dissolved therein an herbal medicinal agent and/or an analgesic agent, wherein the composition is effective when delivered to the mucosal membrane.

The invention provides a composition comprising an aqueous medium having dispersed or dissolved therein an analgesic such as, for example, white willow bark, aspirin, ibuprofen, naproxen, and any combination thereof in an amount of from about 0.001% to about 0.35% by weight; and feverfew dried plant (e.g., leaf) particles dispersed or dissolved in the aqueous medium having a concentration of about 0.001 to 2.0% in the aqueous medium. In one aspect, the feverfew is present at a concentration of about 0.01% to 0.35%. Typically the aqueous medium will comprise water. The composition may further comprise an agent selected from the group consisting of butterbur extract, goldenseal extract, dandelion extract, polyporous extract, ascorbic acid, potassium sorbate, and any combination thereof, as well as a material selected from the group consisting of a surfactant, a vitamin, a vitamin derivative, a wetting agent, a preservative, and an emulsifier (e.g., glycerin).

The invention also provides a method of treating a subject disposed to a headache, toothache, earache, joint pain, backache, abdominal cramps, and the like comprising administering a composition as provided above.

The invention provides a method of treating as subject disposed to a disorder of aches and/or pains by administering to a mucus membrane of the subject a composition comprising an aqueous medium; an analgesic such as, for example, white willow bark, aspirin, ibuprofen, and naproxen in an amount of from about 0.001% to about 0.35% by weight; and feverfew dried plant (e.g., leaf) particles dispersed or dissolved in the aqueous medium having a concentration of about 0.001 to 2.0% in the aqueous medium, wherein the composition is administered in an amount effective to treat or reduce the severity of the aches and/or pains. The method includes administering the composition to the mucus membrane of the sinus cavity and the mouth (e.g., the sublingual space). Thus, the invention can be used to treat headaches (including migraines), premenstrual syndrome (PMS), back pain, earaches, toothaches, and sports-associated pains or aches.

The invention further provides a composition comprising a sprayable aqueous medium having dispersed or dissolved therein an analgesic such as, for example, white willow bark, butterbur extract, aspirin, ibuprofen, and naproxen in an amount of from about 0.001% to about 0.35% by weight of the aqueous carrier, wherein the sprayable aqueous medium is tolerant to mucus membranes.

Other features, objects, and advantages of the invention will be apparent from the description and from the claims.

DETAILED DESCRIPTION

The interest in homeopathic and/or herbal medicines has increased recently due in part to the lower cytotoxicity associated with such medications. Homeopathy is commonly used to mean a system of medicine based on the use of infinitesimal doses of medicines capable of producing symptoms similar to those of the disease treated. By stimulating a subject's natural defenses (i.e., increasing the symptoms) the subject will be motivated or directed towards homeostasis, since one's symptoms are actually efforts of the organism to reestablish homeostasis or balance. Homeopathic treatment encompasses some forms of natural materials including plant extracts and the like. However, some natural plant extracts are not necessarily homeopathic treatments as the extracts themselves do not stimulate disease or disorder symptoms but rather inhibit their onset or severity.

Traditionally the delivery of herbal medicines/therapeutics has been by oral administration through the gastrointestinal tract in the form of tablets or by edible leaves, teas, tinctures, or extracts. The degradative nature of the gastrointestinal tract results in the degradation of the active ingredients in many herbal medicines and therapeutic agents (e.g., analgesics). In order to overcome the degradative processes inherent in oral administration, the amounts and concentrations of herbal medicines, including active ingredients, are increased such that a desired amount of the herbal active ingredient is available to treat the subject once it traverses the gastrointestinal tract. However, such an increase in concentrations and amounts may cause additional side-effects including gastrointestinal discomfort, oral sores, and the like.

The invention provides methods and compositions that utilize small amounts of herbal medicines. The routes of administration used in the methods and compositions of the invention do not require excessive amounts of the herbal medicine or active ingredient. The invention provides compositions for administration to a mucus membrane of a subject including, for example, the sinonasal cavity or oral mucosa (e.g., sublingual space). The mucosal tissue does not contain the acids and enzymes present in the gastrointestinal tract. Thus, the herbal medicines disclosed herein, as well as the active ingredients thereof, are readily available for absorption into the blood stream and related tissues of the subject without unwanted degradation. Accordingly, smaller amounts of such herbal medicines and/or active ingredients are useful in order to treat a subject afflicted with a disease or disorder causing aches, pains, and/or discomfort. The smaller amounts used in the compositions and methods of the invention also result in less gastrointestinal discomfort, sores, and the like.

In addition, administration to the mucus membrane results in a faster uptake of the medicinal product and/or active ingredient. Accordingly, any ache, pain, and/or discomfort will not reach the same severity as with gastrointestinal routes of administration due to the rapid uptake of the compositions. The invention provides a number of herbal and traditional medicinal products that may be provided in the compositions of the invention and may be delivered by the routes identified herein.

Herbal medicines include those derived from, for example, feverfew, butterbur, dandelion, white willow bark, and the like. Feverfew (Tanacetum parthenium) is an herb in the Compositae family that has been known to have therapeutic properties (see, Bremness (ed.), "Herbs," (1990), pp. 91:185–186 and Castleman, "The Healing Herbs," (1991), pp. 173–176). Parthenolide is believed to be the active ingredient in feverfew and is thought to act by inhibiting the release of the vasoconstrictor serotonin from platelets. Recent studies suggest that parthenolide interacts with and inhibits IkappaB kinase beta (IKKbeta). This kinase subunit is known to play a critical role in cytokine-mediated signaling (see, e.g., Kwok et al., Chem Biol. 8(8):759-66, 2001). Parthenolide's in vitro and in vivo anti-inflammatory activity also appears to be mediated through the alpha-methylene gamma-lactone moiety shared by other sesquiterpene lactones. (Id.). Accordingly, feverfew may assist in migraine headache relief by inhibiting inflammation (e.g., via inhibiting release of inflammatory cytokines) and vasoconstriction/spasm thereby restoring normal blood flow.

Traditionally, feverfew has been administered as a raw leaf, either fresh or frozen, which is taken by chewing, by swallowing pills, tablets, capsules, by taking teas, or alcohol tinctures in which the feverfew is incorporated. It has also been administered as a tea with a concentration of 0.5–1 teaspoonfuls of feverfew per cup of boiling water. However, raw feverfew leaves are bitter and therefore unpleasant to chew and the tea is unpleasant to drink. Some evidence suggests that large amounts of feverfew cause oral ulcers or other irritations to the buccal membranes or mucosal membranes of the body including those of the mouth when taken at such high concentrations. In addition, the administration of feverfew by swallowing of the chewed material, drinking of tea, or swallowing of capsules, pills, or tinctures means that the feverfew must be released and dispersed to the central nervous system or other affected organs through the gastrointestinal system. Consequently, as discussed above, the active ingredients found in feverfew will not be readily available to a person to whom the herb has been administered. This has particularly significant drawback in the treatment of migraine headaches.

In the invention, feverfew is provided by either picking fresh leaves and allowing them to dry to a stage where they can be finely ground or otherwise comminuted, or by obtaining previously dried leaves, whole, or previously ground to a desired size. The dried plant (e.g., leaf) particles are dispersed or dissolved in an aqueous media such as the aqueous medium described herein below. The ground particle size useful in the compositions of the invention is about 0.1–20 $\mu$m, or 0.2–10 $\mu$m, but is typically about 0.2–5 $\mu$m. Alternatively, an extract of feverfew leaves may also be prepared by steam distillation, expression (hard pressing), or maceration. A tinture extract can be diluted as appropriate to obtain the desired concentration and/or therapeutic effect. Other methods of preparing the herbal extracts can be found in, "The Homoeopathic Pharmacopoeia," Official Compendium, Jul. 1, 1992, Pharmacopoeia Convention of the American Institute of Homeopathy (Publishers), Falls Church, Va., incorporated herein by reference.

Incorporation of the feverfew particles or extract into the aqueous medium can be performed by dispersing or dissolving the feverfew as a 0.05 to 4% concentration in a lactone solution. When thoroughly mixed and dispersed and/or dissolved, the feverfew will be present at a concentration of about 0.001–2.0%, more commonly about 0.01–0.35%, but typically at about 0.10% by weight.

Similarly, the extract of the Butterbur plant (Petasites hybridus) has been used to treat headaches, neuralgia, and inflammation of the urethra. The extract has been taken orally as a tea or in tablet or gel cap form. The invention provides butterbur extract in an amount that is safe and efficacious for administration to the mucus membranes of a subject. The butterbur extract may be administered alone or in combination with the analgesics and/or herbal medicines (e.g., feverfew) as disclosed herein.

In the invention, butterbur extract is provided by utilizing the rhizomes, roots, and/or leaves of the butterbur plant. In one aspect, the roots and/or leaves are allowed to dry to a stage where they can be finely ground or otherwise comminuted, or by obtaining previously dried roots and/or leaves whole, or previously ground to a desired size. The dried plant (e.g., leaf) and/or root particles are dispersed or dissolved in an aqueous media such as the aqueous medium described herein below. The ground particle size useful in the compositions of the invention is about 0.1–20 $\mu$m, or 0.2–10 $\mu$m, but is typically about 0.2–5 $\mu$m. Alternatively an extract of the roots and/or leaves may also be prepared by steam distillation, expression (hard pressing), or maceration.

Incorporation of the butterbur particles or extract into the aqueous medium can be performed by dispersing or dissolving the butterbur as a 0.05 to 4% concentration in a lactone solution. When thoroughly mixed and dispersed and/or dissolved, the butterbur will be present at a concentration of about 0.001–2.0%, more commonly about 0.01–0.35%, but typically at about 0.10% by weight.

In addition, a number of natural analgesic and antiinflammatory agents exist. White willow bark (a member of the sialix sp.), also known as natural aspirin, has been used in the treatment of pain, fever and as a topical antiseptic. An active ingredient in the white willow bark is salicin, which is converted by the body to acetylsalicylic acid, or aspirin. Although white willow bark is believed to act in a manner similar to aspirin by blocking prostaglandin synthesis, it is efficacious at a lower blood level than aspirin. Recent studies have reported a peak plasma level of 10 mM/L following administration of 1,360 mg extract containing 240 mg salicin. This plasma level is below that of 130 mM/L that occurs following the administration of 500 mg aspirin, a dose common for analgesic and antipyretic activity (see, Schmid et al. Eur J Clin Pharmacol. 57(5):387-91, 2001). In addition sodium salicylates may act by inhibiting the function of neutrophils, the most abundant cell associated with inflammation. Moreover, salicylates that lack an acetyl group, such as those present in white willow bark, do not inhibit aggregation of platelets at physiologically relevant concentrations (see, Krivoy et al., Planta Med. 67(3):209-12, 2001).

In the invention, white willow bark may be dried and ground in a manner similar to the feverfew leaves. The formulation is adjusted to contain 15% salicin. When thoroughly mixed and dispersed and or dissolved in the aqueous medium of the invention the white willow bark will commonly be present at a concentration of about 0.001–2.0% (e.g., about 0.05%), but is typically about 0.01–0.35% by weight.

In another aspect of the invention, nonsteroidal antiinflammatory drugs (NSAIDs), such as, for example, aspirin, ibuprofen (Motrin, Advil, Rufen, others), naproxen, and the like; may be prepared and delivered in accordance with the methods of the invention. Such NSAIDS may be delivered either alone to the mucosal membranes or in combination with one or more other NSAIDs or herbal medicines and/or active ingredients thereof. The compositions and methods of delivery comprising the antiinflammatory agents listed herein provide advantages including, for example, rapid uptake through the mucosal membrane of a subject as well as a need for smaller doses due to the route of administration.

The invention provides an aqueous medium comprising feverfew, white willow bark, butterbur, other herbal medicines, analgesic (e.g., NSAIDs), or any combination thereof.

Acceptable aqueous vehicles for use in the compositions and methods of the invention include, for example, any liquid solution that is capable of dissolving, or generating a suspension of an herbal medicine and/or an analgesic and which is not toxic to the particular subject receiving the formulation. Examples of acceptable aqueous vehicles include, without limitation, saline, water, and acetic acid.

General methods of formulating an aqueous medium can be found in, for example, "Remington's Pharmaceutical Sciences." For example, formulations for inhalation may contain aqueous solutions comprising, polyoxyethylene-9-lauryl ether, glycocholate, and deoxycholate, or may be oily solutions for administration in the form of nasal drops, or as a gel to be applied intranasally.

The aqueous medium typically comprises water and typically includes other materials such as surfactants, vitamins and vitamin derivatives, antihistamines, wetting agents, preservatives, moisturizers, emulsifiers, odorants, and the like, present in conventional concentrations. Those skilled in the art will have no difficulty in determining suitable materials and concentrations for their known functions. In one aspect a general formulation may comprise: feverfew (4% lactone) 0.10%; NaCl 0.85%; ascorbic acid derivative 0.20%; polyoxyethylene (20) sorbitan monooleate 0.13%; goldenseal 0.05%; ethylenediamine tetraacetic acid (EDTA) 0.025%; and water is then the balance of the composition. Where a saline solution is desirable the aqueous medium may comprise a small amount of dissolved sodium chloride in the aqueous medium. The salt concentration may be in the range of 0.1–2.0% and will preferably be on the order of about 0.65% to 0.9%. The NaCl concentration may vary, but is preferably at a normal physiological NaCl concentration. This general formulation may then be modified to include additional herbal medicines such as white willow bark and the like, and/or an analgesic agent (e.g., an NSAID). For example, the invention includes the following general combinations of herbal medicines in an aqueous medium: (1) feverfew particles or extract combined with dandelion extract; (2) feverfew particles or extract combined with dandelion extract, and white willow bark; and (3) feverfew particles or extract combined with a white willow bark extract. Thus, another formulation of the invention includes: Feverfew 0.05%; goldenseal extract 0.004%; dandelion extract 0.0004%; polyporous extract 0.014%; white willow bark 0.05%; glycerin (1,2,3-propanetriol; glycerol) 25.0%; ascorbic acid 0.43%; potassium sorbate 0.15%; and water is then the balance of the composition. The glycerin may be from any readily available source including natural sources as well as synthetic glycerin. In one aspect, the glycerin is a vegetable glycerin. The glycerin aids in the rapid uptake of the herbal medicines and/or analgesics present in the compositions of the invention. For example, the glycerin may act by promoting vasodilation in the sublingual space thereby increasing the uptake of the herbal medicines and/or analgesics of the invention into the blood stream.

In one aspect, the invention provides methods and composition for buccal and preferably sublingual administration. Sublingual administration offers advantages over other routes of administration. For example, compositions administered to the sublingual space have a rapid onset of action, reach high levels in the blood, avoid the first-pass effect of hepatic metabolism, and avoid exposure of the drug to fluids of the gastrointestinal tract. Additional advantages include easy access to the mucus membrane of the sublingual space so that an active substance contained in a therapeutic composition can be easily applied and localized. Further, there is good potential for prolonged delivery through the sublingual mucosal membrane. M. Rathbone & J. Hadgraft, 74 Int'l J. of Pharmaceutics 9 (1991). Suitable nontoxic pharmaceutically acceptable carriers for use in the composition of the present buccal or sublingual dosages can be found in Remington's Pharmaceutical Sciences, 17th Edition, 1985. In addition, to the aqueous medium comprising the herbal medicine and/or analgesic, lozenges for buccal or sublingual administration may also be used. Formulations for lozenges are described in Modem Pharmaceutics, edited by G. S. Banker and C. T. Rhodes, 1996.

The sublingual mucosa includes the membrane of the ventral surface of the tongue and the floor of the mouth, whereas the buccal mucosa constitutes the lining of the cheek. Both the buccal mucosa and the sublingual mucosa are applicable to the methods and compositions of the invention, however, the sublingual space is typically targeted for delivery of the compositions of the invention. The sublingual mucosa is relatively more permeable than the buccal mucosa, thus giving rapid absorption and acceptable bioavailability of many active substances. Furthermore, the sublingual mucosa is convenient, accessible, and generally well accepted. This route has been investigated clinically for the delivery of a substantial number of drugs. It is a commonly used route for administration of nitroglycerin and is also used for buprenorphine and nifedipine. D. Harris & J. Robinson, 81 J. Pharmaceutical Sci. 1 (1992).

The buccal mucosa is less permeable than the sublingual mucosa. The rapid absorption and high bioavailabilities seen with sublingual administration of drugs is not generally provided to the same extent by the buccal mucosa. D. Harris & J. Robinson, 81 J. Pharmaceutical Sci. (1992) at 2. The permeability of the oral mucosa is probably related to the physical characteristics of the tissues. The sublingual mucosa is thinner than the buccal mucosa, thus permeability is greater for the sublingual tissue. The palatal mucosa is intermediate in thickness, but is keratinized thus lessening its permeability, whereas the other two tissues are not.

The ability of molecules to permeate through the oral mucosa appears to be related to molecular size, lipid solubility, ionization and many other factors. Small molecules, less than about 100 daltons, appear to cross the mucosa rapidly. As molecular size increases permeability decreases rapidly. Lipid-soluble compounds are more permeable through the mucosa than are non-lipid-soluble molecules. In this regard, the relative permeability of molecules seems to be related to their partition coefficients. The degree of ionization of molecules, which is dependent on the $pK_a$ of the molecule and the pH at the membrane surface, also greatly affects permeability of the molecules. Maximum absorption occurs when molecules are unionized or neutral in electrical charge and absorption decreases as the degree of ionization increases. Therefore, charged drugs present a significant challenge to absorption through the oral mucosa.

Forms of delivery of compositions to the buccal mucosa and preferably the sublingual mucosa include delivery by a lozenge, troche, breath freshener, mouthwash, or spray. These methods of delivery work by shedding or admixing the active ingredients in the composition into the saliva, which bathes the tissues of the oral cavity and throat as it passes posteriorly towards the esophagus. Such forms remain in the oral cavity only for short periods of time, generally not more than about 10 to 20 minutes.

Accordingly, in one aspect of the invention, the aqueous medium is designed for delivery to the buccal and/or sublingual mucosa. For example, delivery of the aqueous medium comprising an herbal medicine (e.g., feverfew, white willow bark, and/or butterbur extract) and/or an analgesic (e.g., an NSAID identified herein) may be made by any conventional spray technique or device. Spray administration containers for various types of sublingual sprays are known and typically will be suitable for the invention for delivery of an aqueous composition comprising an herbal medicine (e.g., feverfew, white willow bark, and/or butterbur extract) and/or an analgesic (e.g., an NSAID identified herein). The aqueous medium containing an herbal medicine and/or analgesic will commonly be contained in a small bottle or similar container with a focused nozzle from which the aqueous medium comprising the herbal medicine and/or analgesic can be dispersed as a fine mist to be directed under the tongue. Using ambient air as the propelling agent, one can have the bottle made of a flexible plastic, so that merely squeezing the bottle's side propels the spray out through the nozzle into the sublingual space. Air is also the propelling agent for a pump sprayer, in which the user manipulates a small pump button which pumps air into the container and causes the liquid spray to be emitted on the return stroke. Alternatively, the bottle can be pressurized with a gas that is inert to the user and to the ingredients present in the aqueous medium. The gas will be dissolved under pressure in the container or may be generated by dissolution or reaction of a solid material that forms the gas as a product of dissolution or as a reaction product. Typical gases, which can be used, include nitrogen, argon, and a carbon dioxide.

Typically a subject will spray three to ten sprays at each administration, with the administration being repeated on an as needed basis. During use a subject need merely raise their tongue and direct a spray or drop comprising the formulation of the invention to the space under the tongue. The frequency of administration will be dependent on the nature of the usage. If administration is for relief of a current condition, such as a current headache, toothache, earache, and the like, initial relief effects can be expected within a few minutes of administration. Dosages may be repeated at intervals as the effect wears off, if the headache, toothache, or earache persists. The user will normally discontinue administration once the headache, toothache, or earache subsides. Administration can be resumed at a subsequent time when another headache, toothache, earache, or the like occurs. In another aspect, the compositions of the invention may be administered at similar or smaller dosages and on a regular or less frequent basis to create a prophylactic effect intended to prevent the onset of a headache, toothache, earache, or the like. Aqueous formulations, such as the above formulations, can be administered as drops, spray, aerosols or by any other dosage form. Optionally, the delivering system can be a unit dose delivery system. The volume of solution or suspension delivered per dose can be anywhere from 5 to 400 $\mu l$, typically between 50 to 150 $\mu l$. Delivery quantities of the composition for sublingual use are typically about 100 to 150 $\mu l$ per spray.

In addition, to the treatment of aches and pains, including migraine headaches, the compositions and methods of the invention may be useful in the treatment of epilepsy. Migraine headaches sometimes result in seizures due to suspected changes in blood flow. Similarly, the compositions and methods of the invention may prove useful in treating seizures associated with epilepsy by modulating blood flow.

An airway is any part of the mammalian anatomy that air passes through during respiration including the mouth, nasal passages, trachea, bronchi, and bronchial tubes. Such airways are lined by mucosa and thus are applicable to the methods and compositions of the invention. The administration of an herbal medicine and/or analgesic to the lung airways can be any type of administration that places the therapeutic and/or analgesic in contact with lung airway mucus membrane. Such administration can include, for example, by inhalations, nasal sprays, and nasal irrigations wherein the therapeutic and/or analgesic contacts the lung airway mucus membrane. Typical devices for airway administration include a bulb, an inhaler, a nebulizer, an aerosol canister, a spray can, and a mask.

In another aspect of the invention, the aqueous medium is designed for delivery to the sinonasal cavity. In this aspect, an aqueous spray comprising the herbal medicine and/or analgesic is made to the nasal cavity by any conventional spray technique or device. Spray administration containers for various types of nasal sprays are known and are typically suitable for the delivery of the aqueous medium comprising the therapeutic and/or analgesic of the invention. The aqueous liquid medium containing the feverfew, and other appropriate ingredients will commonly be contained in a small bottle or similar container with a focused nozzle, from which it can be dispersed as a fine mist to be directed into each nostril. Using ambient air as the propelling agent, one can have the bottle made of a flexible plastic, so that merely squeezing the bottle's sides impels the spray out through the nozzle into the nasal cavity. Air is also the propelling agent for a pump sprayer, in which the user manipulates a small pump button which pumps air into the container and causes the liquid spray to be emitted on the return stroke. Alternatively, the bottle can be pressurized with a gas that is inert to the user and to the ingredients of the solution. The gas will be dissolved under pressure in the container or may be generated by dissolution or reaction of a solid material that forms the gas as a product of dissolution or as a reaction product. Typical gases, which can be used, include nitrogen, argon, and carbon dioxide.

Typically a subject will spray two or three sprays in each nostril at each administration, with the administration being repeated on an as needed basis. The frequency of administration will be dependent upon the nature of the usage. If administration is for relief of a current condition, such as a current headache, toothache, earache, or the like initial relief effects can be expected within a few minutes of administration. If such does not occur, a user may administer a second dosage. Dosages may be repeated at intervals as the effect wears off. A user will normally discontinue administration once the ache or pain has subsided. Administration can be resumed at a subsequent time when another headache, toothache, earache, or the like occurs. The nasal spray can be administered regularly in smaller doses and on a less frequent basis, to create a prophylactic effect intended to prevent the onset of headaches, tooth aches, earaches, menstrual cramps, intestinal spasms, or the like. Delivery quantities of the composition for sublingual use are typically about 100 to 150 µl per spray.

The nasal administration of the composition of the invention to the mucus membrane of a subject typically places the agent in contact with nasal-paranasal mucus. Direct administration to the nasal-paranasal anatomies can include, without limitation, nasal irrigations, nasal sprays, nasal inhalations, and nasal packs with, for example, saturated gauze provided that the administered composition contact the nasal-paranasal mucus prior to crossing the epithelium. Any device can be used to directly administer the herbal medicines and/or analgesics to the nasal-paranasal anatomy including, without limitation, a bulb, an inhaler, a canister, a spray can, a nebulizer, and a mask. For example, a 20 mL bulb can be used to irrigate the nasal-paranasal anatomy with an aqueous medium comprising an herbal medicine and/or analgesic. Such an aqueous medium formulation can be stored at −20° C., 0° C., or room temperature. If stored below room temperature, the formulation typically is warmed prior to application to the nasal-paranasal cavities.

As noted above, the particular route of administration can influence the effective amount and duration of treatment with an herbal medicine and/or analgesic composition as well as the frequency of administration. For example, orally administered agents may require higher concentrations to deliver an effective amount to a target area or tissue than administration to the mucus membrane.

Other routes of administration to mucosal tissue of a subject include contacting mucosal tissue of the rectum, vagina, and eyes. For example, to treat abdominal cramping due to pre-menstrual syndrome (PMS) or other disease, disorder, or affliction, or to treat back pain, contacting the mucosal tissue most closely associated with the area may result in an increased relief of symptoms compared to oral analgesics and the like.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising an aqueous medium having dispersed or dissolved therein an analgesic selected from the group consisting white willow bark, aspirin, ibuprofen, naproxen, and any combination thereof in an amount of from about 0.001% to about 0.35% by weight; and feverfew dried plant particles dispersed or dissolved in the aqueous medium having a concentration of about 0.001 to 2.0% in the aqueous medium.

2. The composition of claim 1, wherein the feverfew is present at a concentration of about 0.01% to 0.35%.

3. The composition of claim 1, wherein the feverfew is present at a concentration of 0.10%.

4. The composition of claim 1, wherein the composition further comprises an agent selected from the group consisting of butterbur extract, goldenseal extract, dandelion extract, polyporous extract, ascorbic acid, potassium sorbate, and any combination thereof.

5. The composition of claim 1, further comprising a material selected from the group consisting ot a surfactant, a vitamin, a vitamin derivative, a wetting agent, a preservative, and an emulsifier.

6. The composition of claim 5, wherein the emulsifier is glycerin.

7. The composition of claim 1, wherein the analgesic agent is white willow bark.

8. A method of treating a subject disposed to a headache, comprising administering a composition of any one of claims 1 to 7.

9. A method of treating as subject disposed to a disorder of aches and/or pains, comprising administering to a mucus membrane of the subject a composition comprising:

an aqueous medium;

an analgesic selected from the group consisting white willow bark, aspirin, ibuprofen, naproxen, and any combination thereof in an amount of from about 0.001% to about 0.35% by weight in the aqueous medium; and feverfew dried plant particles dispersed or dissolved in the aqueous medium having a concentration of about 0.001 to 2.0% in the aqueous medium, wherein the composition is administered in an amount effective to treat or reduce the severity of the aches and/or pains.

10. The method of claim 9, wherein the administering is by contacting a mucus membrane of the subject with the composition.

11. The method of claim 10, wherein the mucus membrane is found in the sinonasal cavities or mouth.

12. The method of claim 9, wherein the disorder of aches and/or pains is selected from the group consisting of a headache, a migraine headache, a pre-menstrual syndrome (PMS), and a back pain or ache.

13. The method of claim 9, wherein the disorder of aches and/or pains is a headache.

14. The method of claim 13, wherein the headache is a migraine.

15. The method of claim 9, wherein the administration is to a sinonasal cavity and/or a sublingual space.

16. The method of claim 9, wherein the aches and/or pains are due to pre-menstrual syndrome (PMS).

17. The method of claim 16, wherein the PMS comprises a headache.

18. The method of claim 17, wherein the administration is to a sinonasal cavity and/or a sublingual space.

19. The method of claim 9, wherein the feverfew is present at a concentration of about 0.01% to 0.35%.

20. The method of claim 9, wherein the feverfew is present at a concentration of 0.10%.

21. The method of claim 9, wherein the composition further comprises an agent selected from the group consisting of butterbur extract, goldenseal extract, dandelion extract, polyporous extract, ascorbic acid, potassium sorbate, and any combination thereof.

22. The method of claim 9, further comprising a material selected from the group consisting of a surfactant, a vitamin, a vitamin derivative, a wetting agent, a preservative, and an emulsifier.

23. The method of claim 22, wherein the emulsifier is glycerin.

24. The method of claim 9, wherein the analgesic agent is white willow bark.

25. A nasal spray comprising the composition of any one of claims 1 to 7.

26. A sublingual spray comprising the composition of any one of claims 1 to 7.

* * * * *